US012808873B2

(12) United States Patent
Lee et al.

(10) Patent No.: US 12,808,873 B2
(45) Date of Patent: Nov. 24, 2026

(54) USE OF A STIMULATING AGENT TO ASSAY IMMUNE CELL POTENCY

(71) Applicant: RESEARCH INSTITUTE AT NATIONWIDE CHILDREN'S HOSPITAL, Columbus, OH (US)

(72) Inventors: Dean Anthony Lee, Canal Winchester, OH (US); Aarohi Thakkar, Columbus, OH (US); Mark Hall, Columbus, OH (US); Jennifer Muszynski, Columbus, OH (US)

( * ) Notice: Subject to any disclaimer, the term of this patent is extended or adjusted under 35 U.S.C. 154(b) by 1079 days.

(21) Appl. No.: 17/431,276

(22) PCT Filed: Feb. 14, 2020

(86) PCT No.: PCT/US2020/018377

§ 371 (c)(1),
(2) Date: Aug. 16, 2021

(87) PCT Pub. No.: WO2020/168250

PCT Pub. Date: Aug. 20, 2020

(65) Prior Publication Data

US 2022/0128564 A1 Apr. 28, 2022

Related U.S. Application Data

(60) Provisional application No. 62/805,349, filed on Feb. 14, 2019.

(51) Int. Cl.

| | |
|---|---|
| ***G01N 33/575*** | (2026.01) |
| ***A61K 40/15*** | (2025.01) |
| ***A61K 40/42*** | (2025.01) |
| ***G01N 33/68*** | (2006.01) |

(52) U.S. Cl.

CPC ......... *G01N 33/5758* (2026.01); *A61K 40/15* (2025.01); *A61K 40/42* (2025.01); *G01N 33/6863* (2013.01)

(58) Field of Classification Search

CPC ......... G01N 33/57484; G01N 33/6863; G01N 2800/52; G01N 33/5047; A61K 39/4613; A61K 39/4644; A61K 35/17; A61K 39/4611; A61K 2121/00; A61K 39/4614; A61K 39/4631; A61K 2300/00; A61K 40/15; A61K 40/42; A61K 40/11; A61K 40/17; A61K 40/31; C07K 14/54; A61P 35/00

See application file for complete search history.

(56) References Cited

U.S. PATENT DOCUMENTS

| | | | |
|---|---|---|---|
| 4,778,750 | A | 10/1988 | Gottlieb |
| 5,363,860 | A | 11/1994 | Nakao et al. |
| 5,569,585 | A | 10/1996 | Goodwin et al. |
| 5,773,232 | A | 6/1998 | Wier |
| 8,771,971 | B2 | 7/2014 | Norin |
| 9,623,082 | B2 | 4/2017 | Copik et al. |
| 2001/0006789 | A1 | 7/2001 | Maino et al. |
| 2007/0098722 | A1 | 5/2007 | Bottazzi et al. |
| 2010/0221712 | A1 | 9/2010 | Radford et al. |
| 2010/0323368 | A1 | 12/2010 | De Romeuf et al. |
| 2012/0070450 | A1 | 3/2012 | Ishikawa et al. |
| 2014/0017713 | A1 | 1/2014 | Lee et al. |
| 2016/0045551 | A1 | 2/2016 | Brentjens et al. |
| 2017/0333479 | A1 | 11/2017 | Copik et al. |
| 2018/0155690 | A1 | 6/2018 | Park et al. |
| 2018/0340021 | A1 | 11/2018 | Short |
| 2019/0083534 | A1 | 3/2019 | Brentjens et al. |
| 2019/0350985 | A1 | 11/2019 | Kurtzberg et al. |

FOREIGN PATENT DOCUMENTS

| | | | |
|---|---|---|---|
| CN | 105602903 | A | 5/2016 |
| CN | 106659742 | A | 5/2017 |
| CN | 107206100 | A | 9/2017 |
| JP | 2010521680 | A | 6/2010 |
| JP | 2014510517 | A | 5/2014 |
| JP | 7649244 | B2 | 3/2025 |
| RU | 2293993 | C1 | 2/2007 |
| RU | 2015140811 | A | 4/2017 |
| WO | 2005/057217 | | 6/2005 |
| WO | 2006082391 | A1 | 8/2006 |
| WO | 2008/137031 | | 11/2008 |
| WO | 2014005072 | A1 | 1/2014 |
| WO | 2014/207009 | | 12/2014 |
| WO | 2016069607 | A1 | 5/2016 |
| WO | 2017/141243 | A1 | 8/2017 |
| WO | 2018/005712 | A1 | 1/2018 |
| WO | 2020168250 | A1 | 8/2020 |

OTHER PUBLICATIONS

Romee et al. Cytokine-induced memory-like natural killer cells exhibit enhanced responses against myeloid leukemia. Sci Transl Med. Sep. 21, 2016;8(357):357ra123. (Year: 2016).*

Fang et al. NK cell-based immunotherapy for cancer. Semin Immunol. Jun. 2017;31:37-54. (Year: 2017).*

Becker et al. Selection and expansion of natural killer cells for NK cell-based immunotherapy. Cancer Immunol Immunother. Apr. 2016;65(4):477-84. (Year: 2016).*

Granzin M, Stojanovic A, Miller M, Childs R, Huppert V, Cerwenka A. Highly efficient IL-21 and feeder cell-driven ex vivo expansion of human NK cells with therapeutic activity in a xenograft mouse model of melanoma. Oncoimmunology. Aug. 5, 2016;5(9):e1219007. (Year: 2016).*

(Continued)

*Primary Examiner* — Julie Wu
*Assistant Examiner* — Amber K Faust
(74) *Attorney, Agent, or Firm* — Watts Law, LLC; Samantha R. Smart

(57) ABSTRACT

A method of determining the potency of an immune cell is described. The method includes the steps of contacting an immune cell with an effective amount of an stimulating agent (for example, phytohemagglutinin (PHA)) and detecting the amount of a cytokine produced by the immune cell. Kits for assaying immune cell potency are also described. Potency assays are important for satisfying the FDA requirements for new biological agents, such as immunotherapeutic cells. Methods of using potent immune cells as an immunotherapeutic treatment are described.

14 Claims, 10 Drawing Sheets

(56) References Cited

OTHER PUBLICATIONS

Imai C, Iwamoto S, Campana D. Genetic modification of primary natural killer cells overcomes inhibitory signals and induces specific killing of leukemic cells. Blood. Jul. 1, 2005;106(1):376-83. doi: 10.1182/blood-2004-12-4797. (Year: 2005).*

Bonanno, G., Mariotti, A., Procoli, A et al. Interleukin-21 induces the differentiation of human umbilical cord blood CD34-lineage-cells into pseudomature lytic NK cells. BMC Immunol 10, 46 (2009). (Year: 2009).*

English translation of Colombian Office Action issued in Colombian Application No. NC2021/0011986, mailed Oct. 6, 2023.

English translation of Colombian Office Action issued in Colombian Application No. NC2021/0012002, mailed Oct. 12, 2023.

English translation of Russian Office Action issued in Russian Application No. 2021125899/04, mailed Nov. 15, 2023.

English translation of Japanese Office Action issued in Japanese Application No. 2021-547349, mailed Dec. 5, 2023.

Klöß et al., Optimization of Human NK Cell Manufacturing: Fully Automated Separation, Improved Ex Vivo Expansion Using IL-21 with Autologous Feeder Cells, and Generation of Anti-CD123-CAR-Expressing Effector Cells, Hum Gene Ther. vol. 28(10):897-913.

English translation of Russian Office Action issued in Russian Application No. 2021125901/10, mailed Dec. 28, 2023.

English translation of Japanese Office Action issued in Japanese Application No. 2021-547364, mailed Jan. 9, 2024.

English translation of Chinese Office Action issued in Chinese Application No. 2020800145894, mailed Jan. 11, 2024.

Office Action issued in Israel Application No. 285578, mailed Dec. 26, 2023.

International Preliminary Report on Patentability issued for Application No. PCT/US2020/018377, dated Aug. 26, 2021.

International Preliminary Report on Patentability issued for Application No. PCT/US2020/018384, dated Aug. 26, 2021.

International Search Report and Written Opinion issued in PCT/US2020/018384, dated May 7, 2020, 13 pages.

Yu et al. "CD69 enhances immunosuppressive function of regulatory T-cells and attenuates colitis by prompting IL-10 production," Cell Death & Disease, Sep. 5, 2018 {Sep. 5, 2018), vol. 9, No. 905, pp. 1-14.

Becker, Petra SA, et al. "Selection and expansion of natural killer cells for NK cell-based immunotherapy." Cancer Immunology, Immunotherapy 65.4 (2016): 477-484.

Rezvani, Katayoun, and Rayne H. Rouce. "The application of natural killer cell immunotherapy for the treatment of cancer." Frontiers in immunology 6 (2015): 578.

Koepsell, Scott A., Jeffrey S. Miller, and David H. McKenna Jr. "Natural killer cells: a review of manufacturing and clinical utility." Transfusion 53.2 (2013): 404-410.

Darzynkiewicz, Z., et al. "Lymphocyte stimulation: a rapid multiparameter analysis." Proceedings of the National Academy of Sciences 73.8 (1976): 2881-2884.

Klein, Eva, et al. "Properties of the K562 cell line, derived from a patient with chronic myeloid leukemia." International journal of cancer 18.4 (1976): 421-431.

English translation of Chinese Office Action issued in CN202080014589.4, mailed Mar. 24, 2023.

English translation of Search Report issued in RU2021125901/10, mailed Jul. 14, 2023.

Roitt I. et al. Immunology, Moscow, "Mir", 2000, pp. 4-6. English translation.

Abbas A. K., Murphy K. M., Sher A. Functional diversity of helper T lymphocytes. (Engl.) // Nature. Oct. 31, 1996 (vol. 383, No. 6603). pp. 787-793.

Hou, H. et al., Establishment of the Reference Intervals of Lymphocyte Function in Healthy Adults Based on IFN-γ Secretion Assay upon Phorbol-12-Myristate-13-Acetate/Ionomycin Stimulation. Frontiers in Immunology, Feb. 7, 2018, vol. 9, No. 172, pp. 1-11.

English translation of Office Action issued in Indonesian Application No. P00202107491, mailed Apr. 4, 2023.

English translation of Office Action issued in Indonesian Application No. P00202107499, mailed Mar. 30, 2023.

Search Report and Written Opinion issued in Singapore Application No. 11202108604W, mailed May 4, 2023.

Admyre, C. et al., Direct exosome stimulation of peripheral human T cells detected by ELISPOT. European Journal of Immunology, Jul. 1, 2006, vol. 36, No. 7, pp. 1772-1781.

Wahlgren, J. et al., Activated Human T Cells Secrete Exosomes That Participate in IL-2 Mediated Immune Response Signaling. PLoS ONE, Nov. 16, 2012, vol. 7, No. 11, pp. e49723.

English translation of Office Action issued in Russian Application No. 2021125899, mailed Jun. 26, 2023.

Search Report and Written Opinion issued in Singapore Application No. 11202107973P, mailed May 4, 2023.

Dileep P. et al. Immunostimulation of dendritic cells by cationic liposomes. Molecular Membrane Biology, 2006, V.23 (5), pp. 385-395.

International Search Report and Written Opinion mailed May 22, 2020 in PCT/US2020/018377 (9 pages).

Foltz et al., "TGFB Imprinting During Activation Promotes Natural Killer Cell Cytokine Hypersecrection," Cancers (Basel), Nov. 5, 2018, vol. 10, Iss. 11, pp. 1-19.

Viaud et al: "Dendritic Cell-Derived Exosomes Promote Natural Killer Cell Activation and Proliferation : A Role for NKG2D Ligands and IL-15Rα"PLOS ONE, vol. 4, No. 3, Mar. 25, 2009.

Lieberman et al: "An Uncoupling of Canonical Phenotypic Markers and Functional Potency of Ex Vivo-Expanded Natural Killer Cells" Frontiers in Immunology, vol. 9, Feb. 2, 2018.

Oyer et al: "Generation of Highly Cytotoxic Natural Killer Cells for Treatment of Acute Myelogenous Leukemia Using a Feeder-Free, Particle-Based Approach" Biology of Blood and Marrow Transplantation, Kluge Carden Jennings Publishing, vol. 21 , No. 4, Jan. 6, 2015.

Oyer et al: "Natural killer cells stimulated with PM21 particles expand and biodistribute in vivo: Clinical implications for cancer treatment" Cytotherapy, vol. 18, No. 5, May 1, 2016.

Oyer J Let Al : EX21-exosomes", Cytotherapy "NK cell expansion with vol. 20 , No. S5, May 1, 2018, Abstract.

Semino et al : "Chapter Thirteen: NK cell-derived cytokines and delivery: NK cell synapses" Natural Killer Cells, Jan. 1, 2010.

Extended European Search Report issued in EP20755195.3, mailed Nov. 9, 2022.

Extended European Search Report issued in EP20756017.8, mailed Nov. 16, 2022.

Shabrish et al: "A Modified NK Cell Degranulation Assay Applicable for Routine Evaluation of NK Cell Function" Journal of Immunology Research, vol. 2016, Jan. 1, 2016, pp. 1-6.

Sullivan et al., Measurement of cytokine secretion, intracellular protein expression, and mRNA in resting and stimulated peripheral blood mononuclear Cells. Nov. 2007. Clin Diagn Lab Immunol;7(6):920-4. (Year: 2007).

Weber et al., The Emerging Landscape of Immune Cell Therapies. Cell. Apr. 2, 2020;181(1):46-62. (Year: 2020).

Ventola, Cancer Immunotherapy, Part 3: Challenges and Future Trends. PT. Aug. 2017;42(8):514-521. (Year: 2017).

Guedan et al., Emerging Cellular Therapies for Cancer. Annu Rev Immunol. Apr. 26, 2019;37:145-171. (Year: 2019).

Sadelain et al., Therapeutic T cell engineering. Nature. May 24, 2017;545(7655):423-431. (Year: 2017).

Office Action issued in U.S. Appl. No. 17/431,270, mailed Oct. 9, 2024.

European Medicines Agency. Guideline on potency testing of cell based immunotherapy medicinal products for the treatment of cancer, Jul. 21, 2016.

Qin et al., Effect of phytohemagglutinin on proliferation and cytotoxicity of cytokine induced killer cells, Zhongguo shi yan xue ye xue za zhi, 118-120, 2005. Machine Translation.

Office Action issued in Israel Application No. 285578, mailed Jan. 8, 2025.

(56) References Cited

OTHER PUBLICATIONS

Denman et al., "Membrane-Bound IL-21 Promotes Sustained Ex Vivo Proliferation of Human Natural Killer Cells", PLoS One, 7(1): e30264, Jan. 18, 2012.
Office Action issued in Canadian Application No. 3129929, mailed Feb. 4, 2025.
Li et al., "Bifacial effects of engineering tumour cell-derived exosomes on human natural killer cells", Experimental Cell Research, pp. 141-150, 2018.
Jiang et al., "Expansion of NK cells by engineered K562 cells co-expressing 4-1BBL and mMICA, combined with soluble IL-21", Cellular Immunology, 10-20, 2014.
Li et al., "Multiple effects of IL-21 on human NK cells in ex vivo expansion", Immunobiology, pp. 876-888, 2015.
Office Action issued in Canadian Application No. 3129843, mailed Feb. 24, 2025.
Non-Final Office Action for U.S. Appl. No. 17/431,270, mailed Aug. 7, 2025, 17 pages.

* cited by examiner

USE OF A STIMULATING AGENT TO ASSAY IMMUNE CELL POTENCY

RELATED APPLICATIONS

This is a national phase application filed under 35 U.S.C § 371 of International Application No. PCT/US2020/018377, filed on Feb. 14, 2020, entitled "USE OF A STIMULATING AGENT TO ASSAY IMMUNE CELL POTENCY," which claims the benefit of U.S. Provisional Application No. 62/805,349, filed Feb. 14, 2019, which are incorporated herein by reference in their entireties.

FIELD

This invention relates to immunotherapy, and more particularly to testing effector function of immune cells.

BACKGROUND

Immunotherapy is the treatment of disease by activating or suppressing the immune system. Cells derived from the immune system may be used to improve immune functionality and characteristics. In recent years, immunotherapy has become of great interest to researchers, clinicians and pharmaceutical companies, particularly in its promise to treat various forms of cancer. Immunomodulatory regimens often have fewer side effects than existing drugs, including less potential for creating resistance when treating microbial disease.

Conventional cancer treatments focus on killing or removing cancer cells with chemotherapy, surgery, and/or radiation. However, the field of therapeutic immune cells is growing rapidly, and can be used in conjunction with or, in some cases, in place of conventional treatments to treat, prevent, or delay the onset of a cancer. Immune effector cells such as lymphocytes, macrophages, dendritic cells, natural killer cells (NK Cell), cytotoxic T lymphocytes (CTL), etc., naturally work together to defend the body against cancer by targeting abnormal antigens expressed on the surface of tumor cells. Recent cancer treatment developments have focused on directing the patient's immune system to attack and destroy tumors. A variety of strategies are in use or are undergoing research and testing.

Adoptive cell transfer (ACT) is the transfer of cells into a patient, and has shown promise against lung, melanoma, and other cancers. The cells may have originated from the patient (autologous) or from another individual (allogenic). Allogeneic therapies involve cells isolated and expanded from a donor separate from the patient receiving the cells. Alternatively, adoptive cell transfer can be used to cultivate and expand autologous, extracted cells in vitro for later transfusion. For example, autologous immune enhancement therapy involves the extraction of a subject's own peripheral blood-derived natural killer cells, cytotoxic T lymphocytes, epithelial cells and other relevant immune cells, the expansion of these cells in vitro, and then the reinfusion of these cells into the subject's body.

In some therapies, cells (for example, T cells) are genetically modified and expanded in vitro before being returned to the same patient. Chimeric antigen receptor T cell therapy (CAR-T) involves harvesting T cells from a subject and then infecting the T cells with a retrovirus that contains a copy of a T cell receptor (TCR) gene. The TCR gene is specialized to recognize tumor antigens (for example, a chimeric antigen receptor, or CAR). The virus integrates the receptor into the T cells' genome. The cells are expanded non-specifically and/or stimulated. The cells are then reinfused and produce an immune response against the tumor cells.

With the approval of first CAR-T therapy, and multiple commercial companies involved in multiple clinical trials, this field has exploded commercially and has shown a promising future for immunotherapies. With the field advancing with new clinical trials every other day, the need for a reliable and reproducible potency test for these therapeutic immune cells has grown ever since. The industry "gold standard" to test effector function of immune cells is the Chromium release assay, which was developed in the 1960s and which is still in use, even with concerns due to the use of radioactive material and variability caused by target tumor cells. The alternative available is the Calcein-based assay, which still has a lot of variability caused by the use of different tumor targets and due to the entrapment of Calcein in apoptotic bodies of tumor targets.

There have been other efforts to develop different ways to see effector function of these immune cells visually, but these methods still use target tumor cells. Other surrogate methods to check the effector function of immune cells is to check the cytokine produced by these cells, for which all conventional methods use target tumor cells to induce cytokine production from immune cells. Use of the target tumor cells adds biological variability to all of these tests due to variability between tumor cell types. Also, these assays require a tedious setup, which introduces batch effect in these assays. Batch effect is caused by target cell conditions, person to person variability in loading of the plate, plate conditions, variability in various reagents, readout variability, etc. There is a clear need for an immune cell potency assay that can remove all of these variabilities and produce reliable and reproducible results.

A reliable and reproducible potency assay is required to evaluate the quality of immune cell therapy products. The approval process is intensely regulated and the drug developers will be required to submit a substantial amount of information regarding the drug product to the regulatory authorities in order to obtain approval. This may include information regarding the potency of the drug product and assays to determine this potency. As required by the FDA (21 CFR 610.10), potency of the cell therapy product should be indicated by appropriate tests to show effector function of these therapeutic immune cells to show potency, which would be measuring relevant cytokine production by these immune cells.

SUMMARY

The details of one or more embodiments of the invention are set forth in the accompanying drawings and the description below. Other features, objects, and advantages of the invention will be apparent from the description and drawings, and from the claims.

In one aspect, disclosed herein are methods of assaying the potency of an immune cell (such as, for example, a T-cell, a macrophage, a NK cell, NK T cell, CAR T cell, and/or CAR NK cell), comprising contacting an immune cell with an effective amount of a stimulating agent (such as, for example, phytohemagglutinin (PHA), phorbol myristate acetate (PMA)/ionomycin, concanavalin A (Con A), lipopolysaccharide (LPS), and/or pokeweek mitogen (PWM)) and detecting the amount of one or more cytokines (such as, for example, IL-2, IL-6, IFN-γ, TNF-α, BAFF/TNFSF13B, CD163, CD30/TNFRSF8, Chitinase 3-like 1, gp130, IFN-α2, IL-6Rα, IL-8, IL-10, IL-11, IL-12(p40), IL-12(p70), IL-20, IL-22, IL-26, IL-29/IFN-11, IL-32, IL-34, IL-35, MMP-1, Osteocalcin, OPN, Pentraxin-3, TNF-R1, TNF-R2, TSLP, GM-CSF, MIP-1α, MIP-1β, RANTES, and/or TWEAK/TNFSF12) produced by the immune cell. In one aspect, the method can further comprise comparing the amount of cytokine produced to the cytokine potency level required for use of the immune cell in immunotherapy.

Also disclosed herein are methods of assaying the potency of an immune cell of any preceding aspect, wherein the amount of cytokine is detected using an immunoassay (such as, for example, ELISA, intracellular cytokine staining, ELISpot, flow cytometry, Luminex xMAP®, quantitative PCR (including, but not limited to qRT-PCR), and/or bead array).

In one aspect, disclosed herein are methods of assaying the potency of an immune cell of any preceding aspect wherein the immune cell is contacted with an effective amount of a stimulating agent (such as, for example, PHA, PMA/ionomycin, Con A, LPS and/or PWM) for at least 5, 6, 7, 8, 9, 10, 15, 20, 25, 30, 35, 40, 45, 50, 55, 60, 65, 70, 75, 80, 85, 90, 95, 100, 105, 110, 115, 120, 150 minutes, 3, 4, 5,6 7, 8, 9, 10, 11, 12, 13, 14, 15, 16, 17, 18, 19, 20, 21, 22, 23, 24, 30, 32, 36, 42, 48, 60 hours, 3, 4, 5, 6, 7, 8, 9, 10, 11, 12, 13, 14, 15, 16, 17, 18, 19, 20, 21, 22, 23, 24, 25, 26, 27, 28, 29, 30, 31, 45, 60, 61, 62 days, 3, 4, 5, or 6 months.

Also disclosed herein are methods of assaying the potency of an immune cell of any preceding aspect, wherein the stimulating agent (such as, for example, PHA, PMA/ionomycin, Con A, LPS and/or PWM) is provided at a concentration of 1.0 μg/mL to 1000 μg/mL, including, but not limited to a concentration of 5 μg/mL to 15 μg/mL.

In one aspect, disclosed herein are kits for assaying the potency of an immune cell (such as, for example, a T-cell, a macrophage, a NK cell, NK T cell, CAR T cell, and/or CAR NK cell), comprising a container (such as, for example, a microcentrifuge tube) including an effective amount of a stimulating agent (such as, for example, PHA, PMA/ionomycin, Con A, LPS and/or PWM) and a buffer suitable for immune cells. In some aspect, the kit can further comprise instructions for using the kit to stimulate cytokine production by an immune cell Also disclosed herein are kits for assaying the potency of an immune cell of any preceding aspect, wherein the stimulating agent (such as, for example, PHA, PMA/ionomycin, Con A, LPS and/or PWM) is provided at a concentration of 1.0 μg/mL to 1000 μg/mL, including, but not limited to a concentration of 5 μg/mL to 15 μg/mL.

In one aspect, disclosed herein are immunotherapy method comprising a) performing the method of assaying the potency of an immune cell (such as, for example, a T-cell, a macrophage, a NK cell, NK T cell, CAR T cell, and/or CAR NK cell) of any preceding aspect on multiple immune cells to determine the potency of each immune cell; b) selecting at least one potent immune cell based on the amount of cytokine (such as, for example, IL-2, IL-6, IFN-γ, TNF-α, BAFF/TNFSF13B, CD163, CD30/TNFRSF8, Chitinase 3-like 1, gp130, IFN-α2, IL-6Rα, IL-8, IL-10, IL-11, IL-12(p40), IL-12(p70), IL-20, IL-22, IL-26, IL-29/IFN-11, IL-32, IL-34, IL-35, MMP-1, Osteocalcin, OPN, Pentraxin-3, TNF-R1, TNF-R2, TSLP, GM-CSF, MIP-1α, MIP-1β, RANTES, and/or TWEAK/TNFSF12) detected; and c) administering a therapeutically effective amount of the potent immune cell to a subject in need thereof as an immunotherapeutic. In one aspect, the method can further comprise extracting the multiple immune cells from an allogeneic or autologous donor prior to assaying the potency of the immune cell.

Also disclosed herein are immunotherapy methods of any preceding aspect further comprising expanding the at least one potent immune cell prior to delivering a therapeutically effective amount of the potent immune cell.

In one aspect, disclosed herein are immunotherapy methods of any preceding aspect further comprising directing the multiple immune cells or the potent immune cell to respond to a specified antigen. In one aspect, the method can further comprise modification of the cell line from which exosomes are derived, or modification of the exosomes themselves, to include a specified antigen to which the immune cells of interest respond (such as, for example, the addition of CD19 to specifically determine the potency of CD19 CAR T cells in a heterogeneous sample).

Also disclosed herein are immunotherapy methods of any preceding aspect further comprising genetically altering the multiple immune cells or the potent immune cell to present a chimeric antigen receptor.

In one aspect, disclosed herein are methods of treating, inhibiting, reducing, preventing, and/or ameliorating a cancer and/or metastasis in a subject comprising a) obtaining one or more immune cells (such as, for example, a T-cell, a macrophage, a NK cell, NK T cell, CAR T cell, and/or CAR NK cell obtained from an allogeneic or autologous donor); b) contacting an immune cell with an effective amount of a stimulating agent (such as, for example, PHA, PMA/ionomycin, Con A, LPS and/or PWM); c) detecting the amount of a cytokine (such as, for example, IL-2, IL-6, IFN-γ, TNF-α, BAFF/TNFSF13B, CD163, CD30/TNFRSF8, Chitinase 3-like 1, gp130, IFN-α2, IL-6Rα, IL-8, IL-10, IL-11, IL-12(p40), IL-12(p70), IL-20, IL-22, IL-26, IL-29/IFN-11, IL-32, IL-34, IL-35, MMP-1, Osteocalcin, OPN, Pentraxin-3, TNF-R1, TNF-R2, TSLP, GM-CSF, MIP-1α, MIP-1β, RANTES, and/or TWEAK/TNFSF12) produced by the immune cell; d) selecting at least one potent immune cell based on the amount of cytokine detected; and e) administering to the subject a therapeutically effective amount of the potent immune cell. In some aspect, the method can further comprise extracting the immune cell from an autologous or allogeneic donor.

Also disclosed herein are methods of treating, inhibiting, reducing, preventing, and/or ameliorating a cancer and/or metastasis of any preceding aspect further comprising expanding the at least one potent immune cell prior to delivering a therapeutically effective amount of the at least one potent immune cell.

Also disclosed herein are methods of determining the identity (such as, for example, differentiating Th1, Th2, Th3, Th9, Th17, effector memory T (Tem) cells, central memory T (Tcm) cells, γδT cells, or regulatory T (Treg) cells, resting NK cells, expanded NK cells) of at least one immune cell or a population of cells on the basis of the cytokines signature associated with that cell type.

DETAILED DESCRIPTION

Figure 1:
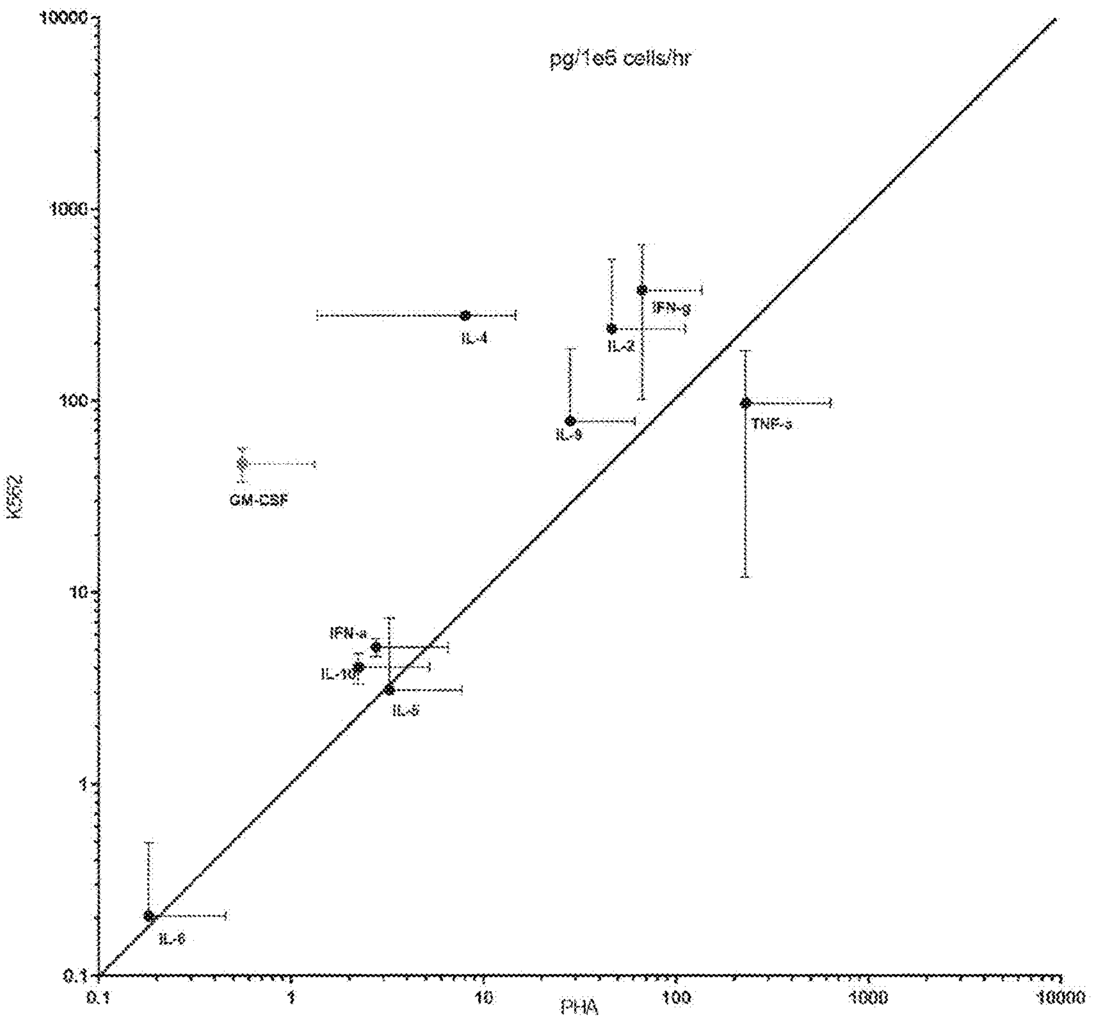
FIG. 1 provides a plot showing the correlation between NK cell cytokine release induced by K-562 tumor cells versus NK cell cytokine release induced by PHA (in pg/million cells/hr).

The present invention provides a method of determining the potency of an immune cell that includes contacting an immune cell with an effective amount of a stimulating agent and detecting the amount of a cytokine produced by the immune cell. While the disclosure is given in the context of cancer immunotherapies, the concepts and innovations disclosed herein may be applied to immunotherapies for other diseases and disorders. For example, an immune cell used in immunotherapy against autoimmune disease, inflammatory diseases or disorders, viral diseases and/or bacterial infections can also be tested for potencies using the assays disclosed herein.

Definitions

For clarification in understanding and ease in reference a list of terms used throughout the brief description section and the remainder of the application has been compiled here. Some of the terms are well known throughout the field and are defined here for clarity, while some of the terms are unique to this application and therefore have to be defined for proper understanding of the application.

As used in the specification and claims, the singular form "a," "an," and "the" include plural references unless the context clearly dictates otherwise. For example, the term "a cell" includes a plurality of cells, including mixtures thereof Where the plural form is used herein, it generally includes the singular.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. Recitations of numerical ranges by endpoints include all numbers subsumed within that range (e.g., 1 to 5 includes 1, 1.5, 2, 2.75, 3, 3.80, 4, 5, etc.). It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that throughout the application, data is provided in a number of different formats and that this data represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

An "increase" can refer to any change that results in a greater amount of a symptom, disease, composition, condition or activity. An increase can be any individual, median, or average increase in a condition, symptom, activity, composition in a statistically significant amount. Thus, the increase can be a 1, 2, 3, 4, 5, 6, 7, 8, 9, 10, 15, 20, 25, 30, 35, 40, 45, 50, 55, 60, 65, 70, 75, 80, 85, 90, 95, or 100% increase so long as the increase is statistically significant.

A "decrease" can refer to any change that results in a smaller amount of a symptom, disease, composition, condition, or activity. A substance is also understood to decrease the genetic output of a gene when the genetic output of the gene product with the substance is less relative to the output of the gene product without the substance. Also for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

The term "therapeutically effective" is intended to qualify the number or amount of an active agent (such as immunotherapeutic cells) which will achieve the goal of decreasing disease severity while avoiding adverse side effects such as those typically associated with alternative therapies. A therapeutically effective amount may be administered in one or more doses. Treatments that are therapeutically effective include treatments that improve a subject's quality of life even if they do not improve the disease outcome per se An "effective amount" generally means an amount which provides the desired local or systemic effect, e.g., effective to stimulate cytokine formation, including achieving the specific desired effects described in this application. For example, an effective amount is an amount sufficient to effectuate a beneficial or desired clinical result.

The term "subject" refers to any individual who is the target of administration or treatment. The subject can be a vertebrate, for example, a mammal. In one aspect, the subject can be human, non-human primate, bovine, equine, porcine, canine, or feline. The subject can also be a guinea pig, rat, hamster, rabbit, mouse, or mole. Thus, the subject can be a human or veterinary patient. The term "patient" refers to a subject under the treatment of a clinician, e.g., physician.

The term "therapeutically acceptable carrier" means a carrier or excipient that is useful in preparing a composition that is generally safe and non-toxic, and includes a carrier that is acceptable for veterinary and/or human use. Intravenous delivery methods will utilize a therapeutically acceptable carrier that is physiologically balanced (for example, at an osmotic and pH level that is safe for intravenous use). As used herein, the term "therapeutically acceptable carrier" encompasses any of the standard carriers, such as saline, Ringers, a phosphate buffered saline solution, water, dextrose in water, and emulsions, such as an oil/water or water/oil emulsion, and various types of wetting agents. As used herein, the term "carrier" encompasses any excipient, diluent, filler, salt, buffer, stabilizer, solubilizer, lipid, stabilizer, or other material well known in the art for use in therapeutic formulations. The therapeutically acceptable carrier also can include preservatives (including cryopreservatives), such as those that would preserve the viability and/or potency of an immune cell. A "therapeutically acceptable carrier" as used in the specification and claims includes both one and more than one such carrier.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

"Administration" to a subject includes any route of introducing or delivering to a subject an agent. Administration can be carried out by any suitable route, including oral, topical, intravenous, subcutaneous, transcutaneous, transdermal, intramuscular, intra joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time or essentially immediately following one another. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration, but are undetectable or detectable at negligible amounts in distal parts of the subject's body. Administration includes self-administration and the administration by another.

"Treat," "treating," "treatment," and grammatical variations thereof as used herein, include the administration of a composition with the intent or purpose of partially or completely preventing, delaying, curing, healing, alleviating, relieving, altering, remedying, ameliorating, improving, stabilizing, mitigating, and/or reducing the intensity or frequency of one or more a diseases or conditions, a symptom of a disease or condition, or an underlying cause of a disease or condition. Treatments according to the invention may be applied preventively, prophylactically, palliatively or remedially. Prophylactic treatments are administered to a subject prior to onset (e.g., before obvious signs of cancer), during early onset (e.g., upon initial signs and symptoms of cancer), or after an established development of cancer. Prophylactic administration can occur for day(s) to years prior to the manifestation of symptoms of a disease or an infection.

The methods and kits disclosed herein utilize a stimulating agent. As used herein, a stimulating agent can be any molecule, peptide, polypeptide, protein, lectin, and/or mitogen that can act as an antigen and/or immunogen to stimulate an immune cell to secrete cytokines. Stimulating agents include but are not limited to phytohemagglutinin (PHA), phorbol myristate acetate (PMA)/ionomycin, concanavalin A (Con A), lipopolysaccharide (LPS), and/or pokeweek mitogen (PWM), peanut agglutinin (PNA), wheat germ agglutinin, and ricin.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

Immune Potency Assay

In one aspect, the invention provides a method of determining the potency of an immune cell. The method includes the steps of contacting an immune cell with an effective amount of a stimulating agent (such as, for example, PHA, PMA/ionomycin, Con A, LPS and/or PWM), and detecting the amount of a cytokine produced by the immune cell. For example, the immune cell can be contacted with a stimulating agent (such as, for example, PHA, PMA/ionomycin, Con A, LPS and/or PWM) by suspending the stimulating agent in a cell medium and exposing the immune cells to the cell medium.

In some embodiments, the method includes the step of comparing the amount of cytokine produced to the cytokine potency level required for use of the immune cell in immunotherapy. A potency assay serves to characterize the product (i.e., immune cells), to monitor lot-to-lot consistency and to assure stability of the product, and should therefore be sufficiently sensitive to detect differences which may impact mechanism of action and function of the product and are thereby of potential clinical importance. The assay can also be used as a predictive biomarker or pharmacodynamic assay for cell-mediated immunotherapy. It is preferable for the potency assay bears the closest possible relationship to the putative physiological/pharmacological activity of the product. The potency assay described herein provides the ability to measure potency value within the product specifications; high sensitivity for detection of differences of potential clinical importance; close relationship with the mechanism of action and putative physiological/pharmacological activity of the product. Preferably, the potency assay also satisfies the following secondary criteria: sufficiently low intra- and inter-assay variation (to obtain precision needed to support product specifications); sufficient robustness; and amenable to high-throughput analysis. In some embodiments, the assay is used as a clinical assay to quantify T cell, macrophage, NK cell, NK T cell, CAR T cell, and/or CAR NK cell function (diagnostic for NK cell immune deficiency, biomarker for monitoring immunosuppressant or immune-activator effectiveness).

As noted above, the disclosed methods provide for determining the potency of an immune cell. Immune cells, as defined herein, are any cells of the immune system that produce cytokines (i.e., cytokine-producing immune cells). Examples of cytokine-producing immune cells include lymphocytes, neutrophils, macrophages, and natural killer cells. Lymphocytes include both B-cells and T-cells (including CD4 and CD8 T cells). In one aspect, the immune cell can comprise a tumor infiltrating lymphocyte (TIL), T cell, a macrophage, natural killer (NK) cell, NK T cell, chimeric antigen receptor (CAR) T cell, and/or CAR NK. The immune cells can be obtained from cell culture, or can be obtained from a subject (such as, for example, an allogenic donor or autologous donor).

In some embodiments, the immune cell is a T-cell. T-cells play a central role in cell-mediated immunity, and can be distinguished from other lymphocytes, such as B cells and natural killer cells, by the presence of a T-cell receptor on the cell surface. Examples of T-cells include T helper cells (TH cells), cytotoxic T cells (TC cells), memory T cells, regulatory or “suppressor” T cells, and Natural killer T cells (NKT cells, which are distinct from NK cells and recognize a glycolipid antigen rather than peptides presented by the MHC molecule. Different types of T-cells differ from each other in their pattern of cytokine production). T cells can be CD4 or CD8 T cells. Additionally, T cells can comprise chimeric antigen receptor (CAR) T cells or tumor infiltrating lymphocytes (TILs).

In some embodiments, the immune cell is an NK cell. Natural Killer Cells are a type of cytotoxic lymphocyte of the immune system. NK cells provide rapid responses to virally infected cells and respond to transformed cells. Typically, immune cells detect peptides from pathogens presented by Major Histocompatibility Complex (MHC) molecules on the surface of infected cells, triggering cytokine release, causing lysis or apoptosis. NK cells are unique, however, as they have the ability to recognize stressed cells regardless of whether peptides from pathogens are present on MHC molecules. They were named “natural killers” because of the initial notion that they do not require prior activation in order to kill target. NK cells are large granular lymphocytes (LGL) and are known to differentiate and mature in the bone marrow from where they then enter into the circulation. In some aspect, the NK cell can be a CAR NK cell.

Thus, in one aspect, disclosed herein are methods of assaying the potency of an immune cell (such as, for example, a T-cell, a macrophage, a NK cell, NK T cell, CAR T cell, and/or CAR NK cell), comprising contacting an immune cell with an effective amount of a stimulating agent (such as, for example, PHA, PMA/ionomycin, Con A, LPS and/or PWM) and detecting the amount of one or more cytokines produced by the immune cell. In one aspect, the method can further comprise comparing the amount of cytokine produced to the cytokine potency level required for use of the immune cell in immunotherapy.

The assay includes the step of detecting the amount of a cytokine produced by the immune cell after stimulating the immune cells with the stimulating agent. As used herein, the term “cytokine” refers to a small protein (~5-20 kDa) that is important in cell signaling, and in particular immunomodulation that can be produced by an immune cell. Examples of cytokines include chemokines, interferons, interleukins, lymphokines, and tumor necrosis factors. The cytokines detected can include cytokines known to be produced by the immune cells being evaluated, or the detection can encompass a wider variety of cytokines, including cytokines not known to be produced by the immune cells.

In some embodiments, the cytokines being detected include cytokines known to be produced by T-cells or Natural Killer cells. In some embodiments, the cytokines include those known to be produced by T-cells. T-cells include Th1 and Th2 cells; Th1 cells predominantly produce interferon (IFN)-γ (IFN-γ), tumor necrosis factor (TNF)-α

(TNF-α), and IL-2; Th2 cells produce interleukin (IL)-2 (IL-2), IL-4, IL-5, IL-6, IL-9, IL-13, and IL-22. Examples of cytokines produced by stimulated Natural Killer cells include IL-1α, IL-1β, IL-2, IL-5, IL-8, IL-10, IL-13, IFN-γ, TNF-α, granulocyte-macrophage colony-stimulating factor (GM-CSF), leukemia inhibitory factor (LIF), and the chemokines macrophage inflammatory protein (MIP)-1α (MIP-1α), MIP-1β, and RANTES. Other cytokines useful to determine the potency of an immune cell include, but are not limited to B cell activating factor/tumor necrosis factor (TNF) ligand superfamily member 13B (BAFF/TNFSF13B), cluster of differentiation (CD) 163 (CD163), CD30/TNFRSF8, Chitinase 3-like 1, gp130, IFN-α2, IL-6Rα, IL-11, IL-12(p40), IL-12(p70), IL-20, IL-26, IL-29/IFN-11, IL-32, IL-34, IL-35, matrix metalloproteinase-1 (MMP-1), Osteocalcin, Osteopontin (OPN), Pentraxin-3, tumor necrosis factor (TNF)-receptor 1 (TNF-R1), TNF-R2, thymic stromal lymphopoetin (TSLP), or TNF-related weak inducer of apoptosis (TWEAK)/TNF superfamily member 12 (TWEAK/TNFSF12). Thus, in one aspect, disclosed herein are methods of assaying the potency of an immune cell (such as, for example, a T-cell, a macrophage, a NK cell, NK T cell, CAR T cell, and/or CAR NK cell), comprising contacting an immune cell with an effective amount of a stimulating agent (such as, for example, phytohemagglutinin (PHA), phorbol myristate acetate (PMA)/ionomycin, concanavalin A (Con A), lipopolysaccharide (LPS), and/or pokeweek mitogen (PWM)) and detecting the amount of one or more cytokines (such as, for example, IL-2, IL-6, IFN-γ, TNF-α, BAFF/TNFSF13B, CD163, CD30/TNFRSF8, Chitinase 3-like 1, gp130, IFN-α2, IL-6Rα, IL-8, IL-10, IL-11, IL-12(p40), IL-12(p70), IL-20, IL-22, IL-26, IL-29/IFN-11, IL-32, IL-34, IL-35, MMP-1, Osteocalcin, OPN, Pentraxin-3, TNF-R1, TNF-R2, TSLP, GM-CSF, LIF, MIP-1α, MIP-1β, RANTES and/or TWEAK/TNFSF12) produced by the immune cell. disclosed herein are methods of assaying the potency of an immune cell (such as, for example, a T-cell, a macrophage, a NK cell, NK T cell, CAR T cell, and/or CAR NK cell), comprising contacting an immune cell with an effective amount of a stimulating agent (such as, for example, PHA, PMA/ionomycin, Con A, LPS and/or PWM) and detecting the amount of one or more cytokines (such as, for example, IL-2, IL-6, IFN-γ, TNF-α, BAFF/TNFSF13B, CD163, CD30/TNFRSF8, Chitinase 3-like 1, gp130, IFN-α2, IL-6Rα, IL-8, IL-10, IL-11, IL-12(p40), IL-12(p70), IL-20, IL-22, IL-26, IL-29/IFN-11, IL-32, IL-34, IL-35, MMP-1, Osteocalcin, OPN, Pentraxin-3, TNF-R1, TNF-R2, TSLP, GM-CSF, MIP-1α, MIP-1β, RANTES, and/or TWEAK/TNFSF12) produced by the immune cell. In one aspect, the method can further comprise comparing the amount of cytokine produced to the cytokine potency level required for use of the immune cell in immunotherapy. In some embodiments, the levels of a plurality of cytokines are determined. In further embodiments, the cytokine is selected from the group consisting of interleukin-2, interleukin-6, and interferon-γ.

The assay includes the step of detecting the amount of a cytokine produced by the immune cell. A wide variety of methods are known to those skilled in the art for detecting cytokines, which can vary depending on the cytokine being detected. In some embodiments, a method or methods can be used to detect and/or quantify the presence of a plurality of different cytokines. Cytokines can be detected by, for example, the use of specific reagent kits or immunoassays. Cytokines can be detected using kits available from commercial providers such as Miltenyi Biotec™, Luminex, and Thermo Fisher scientific™. Examples of kits suitable for detecting cytokines are the rapid cytokine inspector (CD4/CD8) kit, or the MACSPlex cytokine T/NK kit, which can detect cytokines formed by either T-cells or NK cells, both of which are sold by Miltenyi Biotec™.

In some embodiments, the amount of cytokine is detected using an immunoassay. Immunoassays come in many different formats and variations. Immunoassays may be run in multiple steps with reagents being added and washed away or separated at different points in the assay. Immunoassays include heterogeneous immunoassays, which include multiple steps, and homogenous immunoassays, which involve simply mixing the reagents and sample and making a physical measurement. Immunoassays often make use of a calibrator, which is a solution known to contain the analyte in question, and the concentration of that analyte is generally known. Comparison of an assay's response to a real sample against the assay's response produced by the calibrators makes it possible to interpret the signal strength in terms of the presence or concentration of analyte in the sample. Types of immunoassays include competitive, homogenous immunoassays, competitive heterogenous immunoassays, one-site non-competitive immunoassays, and two-site noncompetitive immunoassays. Immunoassays also include Enzyme-linked immunosorbent assays (ELISA), lateral flow immunoassays, enzyme-linked immunosorbent spot (ELlspot) assays, flow cytometry, intracellular cytokine staining, antibody array assays and bead-based assays, magnetic immunoassays, radioimmunoassays, and quantitative PCR (including, but not limited to qRT-PCR). In one aspect, the assay comprises a Luminex xMAP®.

The method of determining the potency of an immune cell includes the step of contacting an immune cell with an effective amount of a stimulating agent (such as, for example, PHA, PMA/ionomycin, Con A, LPS and/or PWM).

It is understood and herein contemplated that the immune cells must be exposed to the stimulating agent for a period of time to be induced to produce cytokines. In one aspect, disclosed herein are methods of assaying the potency of an immune cell wherein the immune cell is contacted with an effective amount of stimulating agent (such as, for example, PHA, PMA/ionomycin, Con A, LPS and/or PWM) for at least 5, 6, 7, 8, 9, 10, 15, 20, 25, 30, 35, 40, 45, 50, 55, 60, 65, 70, 75, 80, 85, 90, 95, 100, 105, 110, 115, 120, 150 minutes, 3, 4, 5,6 7, 8, 9, 10, 11, 12, 13, 14, 15, 16, 17, 18, 19, 20, 21, 22, 23, 24, 30, 32, 36, 42, 48, 60 hours, 3, 4, 5, 6, 7, 8, 9, 10, 11, 12, 13, 14, 15, 16, 17, 18, 19, 20, 21, 22, 23, 24, 25, 26, 27, 28, 29, 30, 31, 45, 60, 61, 62 days, 3, 4, 5, or 6 months.

Also disclosed herein are methods of assaying the potency of an immune cell of any preceding aspect, wherein the stimulating agent (such as, for example, PHA, PMA/ionomycin, Con A, LPS and/or PWM) is provided at a concentration of 5 μg/mL to 1000 μg/mL, In one aspect, the concentration of the stimulating agent is 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 110, 120, 125, 130, 140, 150, 160, 170, 175, 180, 190, 200, 225, 250, 275, 300, 325, 350, 375, 400, 425, 450, 475, 500, 550, 600, 650, 700, 750, 800, 850, 900, 950, or 1000 μg/mL. In one aspect, the concentration of the stimulating agent is from about 1 μg/mL to 100 μg/mL, 1 μg/mL to 50 μg/mL, 1 μg/mL to 15 μg/mL, or 5 μg/mL to 15 μg/mL.

In one aspect, it is understood and herein contemplated that the same cytokines produced to determine potency of an immune cell can also be used to identify the cells producing the cytokines. Immune cells have distinct expression profiles that well known in the art. Also disclosed herein are methods of determining the identity of at least one immune cell or a population of cells (such as, for example, differentiating Th1, Th2, Th3, Th9, Th17, effector memory T (Tem) cells, central memory T (Tcm) cells, γδT cells, or regulatory T (Treg) cells, resting NK cells, expanded NK cells) on the basis of the cytokines signature associated with that cell type. Accordingly, disclosed herein are methods of identifying an immune cell (such as, for example, a T-cell, a macrophage, a NK cell, NK T cell, CAR T cell, and/or CAR NK cell), comprising contacting an immune cell with an effective amount of a stimulating agent (such as, for example, PHA, PMA/ionomycin, Con A, LPS and/or PWM) and detecting the amount of one or more cytokines (such as, for example, IL-2, IL-6, IFN-γ, TNF-α, BAFF/TNFSF13B, CD163, CD30/TNFRSF8, Chitinase 3-like 1, gp130, IFN-α2, IL-6Rα, IL-8, IL-10, IL-11, IL-12(p40), IL-12(p70), IL-20, IL-22, IL-26, IL-29/IFN-11, IL-32, IL-34, IL-35, MMP-1, Osteocalcin, OPN, Pentraxin-3, TNF-R1, TNF-R2, TSLP, GM-CSF, MIP-1α, MIP-1β, RANTES, and/or TWEAK/TNFSF12) produced by the immune cell; wherein the identity of the immune cell is revealed based on the profile of cytokines expressed.

Kits for Evaluating Immune Cell Potency

Another aspect of the invention provides a kit for determining the potency of an immune cell (such as, for example, a T-cell, a macrophage, a NK cell, NK T cell, CAR T cell, and/or CAR NK cell), comprising a container including an effective amount of a stimulating agent (such as, for example, PHA, PMA/ionomycin, Con A, LPS and/or PWM) and a buffer suitable for immune cells. In some embodiments, the stimulating agent in the kit is provided at a concentration of 5 μg/mL to 1000 μg/mL, In one aspect, the concentration of the stimulating agent is 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 110, 120, 125, 130, 140, 150, 160, 170, 175, 180, 190, 200, 225, 250, 275, 300, 325, 350, 375, 400, 425, 450, 475, 500, 550, 600, 650, 700, 750, 800, 850, 900, 950, or 1000 μg/mL. In one aspect, the concentration of the stimulating agent is from about 1/mL to 100 μg/mL, 1 μg/mL to 50 μg/mL, 1 μg/mL to 15 μg/mL, or 5 μg/mL to 15 μg/mL. In some embodiments, the container is a microcentrifuge tube (such as, for example an Eppendorf microcentrifuge tube). Kits can also include a tool for obtaining a sample from a subject, such as a syringe to obtain a sample including one or more immune cells. A suitable buffer is RPMI.

The kits may also include the components required for conducting an immunoassay, such as a solid phase, to which the antibodies functioning as capture antibodies and/or detection antibodies in a sandwich immunoassay format are bound. The solid phase may be a material such as a magnetic particle, a bead, a test tube, a microtiter plate, a cuvette, a membrane, a scaffolding molecule, a quartz crystal, a film, a filter paper, a disc or a chip. The kit may also include a detectable label that can be or is conjugated to an antibody, such as an antibody functioning as a detection antibody. The detectable label can for example be a direct label, which may be an enzyme, oligonucleotide, nanoparticle chemiluminophore, fluorophore, fluorescence quencher, chemiluminescence quencher, or biotin. Test kits may optionally include any additional reagents needed for detecting the label.

The kit can further include instructions for using the kit to stimulate cytokine production by an immune cell in order to evaluate the potency of the immune cell. In some embodiments, the kit further includes instructions for using the amount of cytokine to determine the potency of the cell. Instructions included in kits can be affixed to packaging material or can be included as a package insert. While the instructions are typically written or printed materials, they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term “instructions” can include the address of an interne site that provides the instructions.

Immunotherapy Methods

The method of determining the potency of an immune cell can be performed prior to the use of the immune cell as an immunotherapeutic agent. For example, the method of determining the potency of one or multiple immune cells can be performed as described above, after which at least one potent immune cell can be selected (based on the amount of cytokine detected) and a therapeutically effective amount of the potent immune cell can be delivered to a subject as an immunotherapeutic. Thus, In one aspect, disclosed herein are immunotherapy methods comprising a) performing the method of assaying the potency of an immune cell (such as, for example, a T-cell, a macrophage, a NK cell, NK T cell, CAR T cell, and/or CAR NK cell) as disclosed herein on multiple immune cells to determine the potency of each immune cell; b) selecting at least one potent immune cell based on the amount of cytokine (such as, for example, IL-2, IL-6, IFN-γ, TNF-α, BAFF/TNFSF13B, CD163, CD30/TNFRSF8, Chitinase 3-like 1, gp130, IFN-α2, IL-6Rα, IL-8, IL-10, IL-11, IL-12(p40), IL-12(p70), IL-20, IL-22, IL-26, IL-29/IFN-11, IL-32, IL-34, IL-35, MMP-1, Osteocalcin, OPN, Pentraxin-3, TNF-R1, TNF-R2, TSLP, GM-CSF, MIP-1α, MIP-1β, RANTES, and/or TWEAK/TNFSF12) detected; and c) administering a therapeutically effective amount of the potent immune cell to a subject in need thereof as an immunotherapeutic. In one aspect, the method can further comprise extracting the multiple immune cells from an allogeneic or autologous donor prior to assaying the potency of the immune cell.

In some embodiments, the immune cells are immunotherapeutic immune cells. Immunotherapeutic immune cells are those that are useful for treatment of diseases such as cancer. Becker et al., Cancer Immunol. Immunother 65, 477-484 (2016). The use of expanded NK cells for treatment of cancer has been described. Rezvani et al., Front Immunol., 6, 578 (2015). Because it is helpful to be able to administer large numbers of immune cells during immunotherapy, in some embodiments the immune cells are expanded immune cells. Expanded immune cells are those that are grown ex-vivo in order to grow a large number of immune cells. In some embodiments, the expanded immune cells are autologous cells that can be easily administered to a subject without provoking an immune response. However, in some embodiments, the expanded immune cells are allogeneic immune cells, in which their inherent alloreactivity can be a benefit. In further embodiments, the expanded immune cells are genetically engineered to include chimeric antigen receptors to help the immune cells target diseased tissue. Preparation of expanded immune cells includes activating and expanding the immune cells. Koepsell et al., Transfusion, 53(2): 404-10 (2013). A number of cytokines (IL-2, IL-12, IL-15, IL-18, IL-21, type I IFNs, and TGF-β) have been shown to be useful for activating and expanding immune cells ex vivo. For example, in some embodiments, the NK cells being evaluated are IL-21 expanded NK cells. Accordingly, in one aspect, disclosed herein are immunotherapy methods further comprising expanding the at least one potent immune cell prior to delivering a therapeutically effective amount of the potent immune cell.

Expansion refers to the ex vivo proliferation of NK cells so that the population of NK cells is increased. NK cells can be expanded, for example, from peripheral blood mononuclear cells. However, NK cells can also be expanded from other types of cells, such as hematopoietic stem cells or progenitor cells. The initial blood or stem cells can be isolated from a variety of different sources, such placenta, umbilical cord blood, placental blood, peripheral blood, spleen or liver. Expansion occurs in a cell culture medium. Suitable cell culture mediums are known to those skilled in the art. The expanded cells can be a provided as a cell line, which is a plurality of cells that can be maintained in cell culture. Thus, in one aspect, disclosed herein are immunotherapy methods further comprising expanding the at least one potent immune cell prior to delivering a therapeutically effective amount of the potent immune cell. In some aspects, the immune cell has been extracted from a subject using known methods prior to performing the method of determining the potency of the immune cell. Alternatively, the immune cell can be sourced from expansion of a cell culture.

In some aspects, an immune cell is directed to respond to a specified antigen (for example, CD19). The immune cell can be directed to respond prior to the method of determining its potency, or after the method of determining its potency. In some embodiments, the immune cell is genetically altered to respond to a specified antigen. The antigen can be a tumor-specific antigen, for example. In some aspects, the immunotherapy methods include genetically altering the immune cells to present a chimeric antigen receptor (either before or after determining the potency of the immune cell). In one aspect, the method can further comprise modification of the cell line from which exosomes are derived, or modification of the exosomes themselves, to include a specified antigen to which the immune cells of interest respond (such as, for example, the addition of CD19 to specifically determine the potency of CD19 CART cells in a heterogeneous sample).

As noted throughout the method of determining the potency of an immune cell can be used as part of an adoptive cell transfer treatment. The potent immune cell can be delivered to a subject using a therapeutically acceptable carrier. Intravenous delivery is conventionally used to deliver immunotherapeutic cells, but other methods can also be considered (direct transplant to a localized area of the body in need of immunotherapy, for example).

The therapeutically effective amount can be determined by comparing the amount of cytokine produced by the immune cell to the cytokine potency level required for use of the immune cell in immunotherapy. It is understood and herein contemplated that the therapeutically effective amount depends on the immune cell being administered, the subject being treated, and the disease, disorder, and/or condition being treated. Those of skill in the art will know the appropriate dosage of immune cells to use that will be therapeutically effective for the subject being treated.

A therapeutically effective amount of a potent immune cell encompasses a plurality of potent immune cells. For example, after selecting at least one potent immune cell, the selected cell can be expanded in vitro to produce a plurality of potent immune cells.

The subject receiving the potent immune cells can be any subject that would benefit from immunotherapy (such as for example a subject with an autoimmune disease, inflammatory diseases or disorders, viral diseases and/or bacterial infections). In some embodiments, the subject can be a cancer patient. In some embodiments, the subject can be an individual at high risk of developing cancer, diagnosed with cancer, being treated for cancer, or recovering from cancer after surgery. In some embodiments, the potent immune cells can be delivered to a subject as a prophylactic agent for preventing, inhibiting, or delaying the onset of cancer or a metastasis.

Methods of Treating a Disease

It is understood and herein contemplated that the potent immune cells identified herein can be used in the treatment of any disease or disorder where adoptive immunotherapy could be used for treatment including, but not limited to autoimmune disease, inflammatory diseases or disorders, viral diseases and/or bacterial infections. Thus, in one aspect, disclosed herein are methods of treating, inhibiting, reducing, preventing, and/or ameliorating a cancer and/or metastasis in a subject comprising a) obtaining one or more immune cells (such as, for example, a T-cell, a macrophage, a NK cell, NK T cell, CAR T cell, and/or CAR NK cell obtained from an allogeneic or autologous donor); b) contacting an immune cell with an effective amount of a stimulating agent (such as, for example, PHA, PMA/ionomycin, Con A, LPS and/or PWM); c) detecting the amount of a cytokine (such as, for example, IL-2, IL-6, IFN-γ, TNF-α, BAFF/TNFSF13B, CD163, CD30/TNFRSF8, Chitinase 3-like 1, gp130, IFN-α2, IL-6Rα, IL-8, IL-10, IL-11, IL-12(p40), IL-12(p70), IL-20, IL-22, IL-26, IL-29/IFN-11, IL-32, IL-34, IL-35, MMP-1, Osteocalcin, OPN, Pentraxin-3, TNF-R1, TNF-R2, TSLP, GM-CSF, MIP-1α, MIP-1β, RANTES, and/or TWEAK/TNFSF12) produced by the immune cell; d) selecting at least one potent immune cell based on the amount of cytokine detected; and e) administering to the subject a therapeutically effective amount of the potent immune cell. In some aspect, the method can further comprise extracting the immune cell from an autologous or allogeneic donor.

It is understood and herein contemplated that it is helpful to be able to administer large numbers of immune cells during immunotherapy, in some embodiments the immune cells are expanded immune cells. Expanded immune cells are those that are grown ex-vivo in order to grow a large number of immune cells. Accordingly, disclosed herein are methods of treating, inhibiting, reducing, preventing, and/or ameliorating an autoimmune disease, inflammatory disease or disorder, viral disease, bacterial infection, cancer and/or metastasis further comprising expanding the at least one potent immune cell prior to delivering a therapeutically effective amount of the at least one potent immune cell.

It is understood and herein contemplated that the disclosed methods of treatment can be used to treat any disease or condition where uncontrolled cellular proliferation occurs including, but not limited to cancer and metastasis. A representative but non-limiting list of cancers that the disclosed methods of using potent immune cells can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, lung cancers such as small cell lung cancer and non-small cell lung cancer, neuroblastoma/glioblastoma, ovarian cancer, skin cancer, liver cancer, melanoma, squamous cell carcinomas of the mouth, throat, larynx, and lung, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon cancer, rectal cancer, prostatic cancer, or pancreatic cancer.

Examples of autoimmune diseases that can be treated using the disclosed methods include, but are not limited to Achalasia, Acute disseminated encephalomyelitis, Acute motor axonal neuropathy, Addison's disease, Adiposis dolorosa , Adult Still's disease, Agammaglobulinemia, Alopecia areata, Alzheimer's disease, Amyloidosis, Ankylosing spondylitis, Anti-GBM/Anti-TBM nephritis, Antiphospholipid syndrome, Aplastic anemia, Autoimmune angioedema, Autoimmune dysautonomia, Autoimmune encephalomyelitis, Autoimmune enteropathy, Autoimmune hemolytic anemia, Autoimmune hepatitis, Autoimmune inner ear disease (AIED), Autoimmune myocarditis, Autoimmune oophoritis, Autoimmune orchitis, Autoimmune pancreatitis, Autoimmune polyendocrine syndrome , Autoimmune retinopathy, Autoimmune urticaria, Axonal & neuronal neuropathy (AMAN), Baló disease, Behcet's disease, Benign mucosal emphigoid, Bickerstaffs encephalitis , Bullous pemphigoid, Castleman disease (CD), Celiac disease, Chagas disease, Chronic fatigue syndrome, Chronic inflammatory demyelinating polyneuropathy (CIDP), Chronic recurrent multifocal osteomyelitis (CRMO), Churg-Strauss Syndrome (CSS), Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Diabetes mellitus type 1, Discoid lupus, Dressler's syndrome, Endometriosis, Enthesitis, Eosinophilic esophagitis (EoE), Eosinophilic fasciitis, Erythema nodosum, Essential mixed cryoglobulinemia, Evans syndrome, Felty syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's encephalopathy, Hashimoto's thyroiditis, Hemolytic anemia, Henoch-Schonlein purpura (HSP), Herpes gestationis or pemphigoid gestationis (PG), Hidradenitis Suppurativa (HS) (Acne Inversa), Hypogammalglobulinemia, IgA Nephropathy, IgG4-related sclerosing disease, Immune thrombocytopenic purpura (ITP), Inclusion body myositis (IBM), Interstitial cystitis (IC), Inflamatory Bowel Disease (IBD), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus nephritis, Lupus vasculitis, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Ord's thyroiditis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Rheumatoid vasculitis, Sarcoidosis, Schmidt syndrome, Schnitzler syndrome, Scleritis, Scleroderma, Sjogren's syndrome, Sperm & testicular autoimmunity, Stiff person syndrome (SPS), Subacute bacterial endocarditis (SBE), Susac's syndrome, Sydenham chorea, Sympathetic ophthalmia (SO), Systemic Lupus Erythematosus, Systemic scleroderma, Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Urticaria, Urticarial vasculitis, Uveitis, Vasculitis, Vitiligo, Vogt-Koyanagi-Harada Disease, and Wegener's granulomatosis (or Granulomatosis with Polyangiitis (GPA)).

The following example is included to demonstrate preferred embodiments of the invention. It should be appreciated by those of skill in the art that the techniques disclosed in the examples, which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE

The assays disclosed herein intend to test the potency of therapeutic immune cells that would address the problems existing for current standard methods, and satisfy the FDA requirements. To achieve this, phytohemagglutinin (PHA) is used as a surrogate to induce cytokine production in immune cells. PHA is used in clinical settings to test the immune response in transplant patients. Inducing cytokine production in therapeutic immune cells using PHA would remove all of the biological and batch variability from the immune cell potency assay. The assay would eliminate the need to have a fully operational research laboratory to test the potency of therapeutic immune cells at multiple clinical infusion sites, and would provide a quicker turnaround time for such tests. It would provide a method to test the effector function of therapeutic immune cells as part of a potency testing requirement set by the FDA.

Testing the Potency of Therapeutic Immune Cells Using PHA as a Stimulatory Agent Use of tumor cells to test effector function of therapeutic immune cells has been a standard practice. These target cells add biological variabilities to the outcomes of assay. Also, this assay set up is more tedious and complicated adding up variabilities due to target condition, plate set up, person-to-person difference in techniques. The therapeutic response of NK cells via comparison of a PHA cytokine assay against a widely use tumor cell (K562) mediated cytokine assay. The levels of cytokine indicate potency of the response from the NK cells.

FIG. 1 shows the correlation of the PHA-induced cytokine assay with the standard K562-induced cytokine assay. The outliers present in FIG. 1 are a result of the variability introduced by using tumor cells. Higher secretion of GM-CSF was detected in the tumor cell mediated assay (GC-CSF is usually secreted by tumor cells). This showed clear advantage of PHA assay by lack of tumor cell introduced variability.

Figure 2:
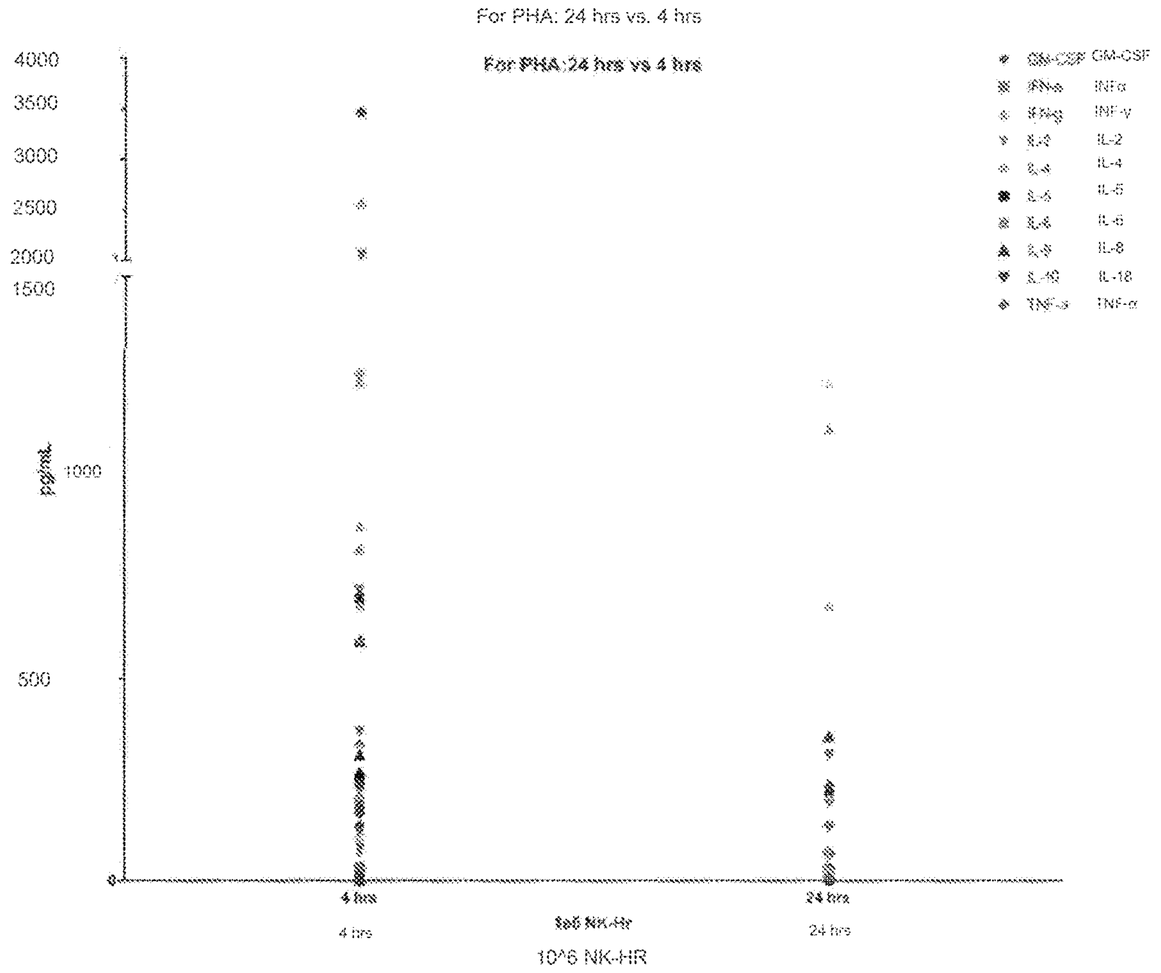
FIG. 2 provides a graph showing an analysis of the results based on incubation time.
Figure 3:
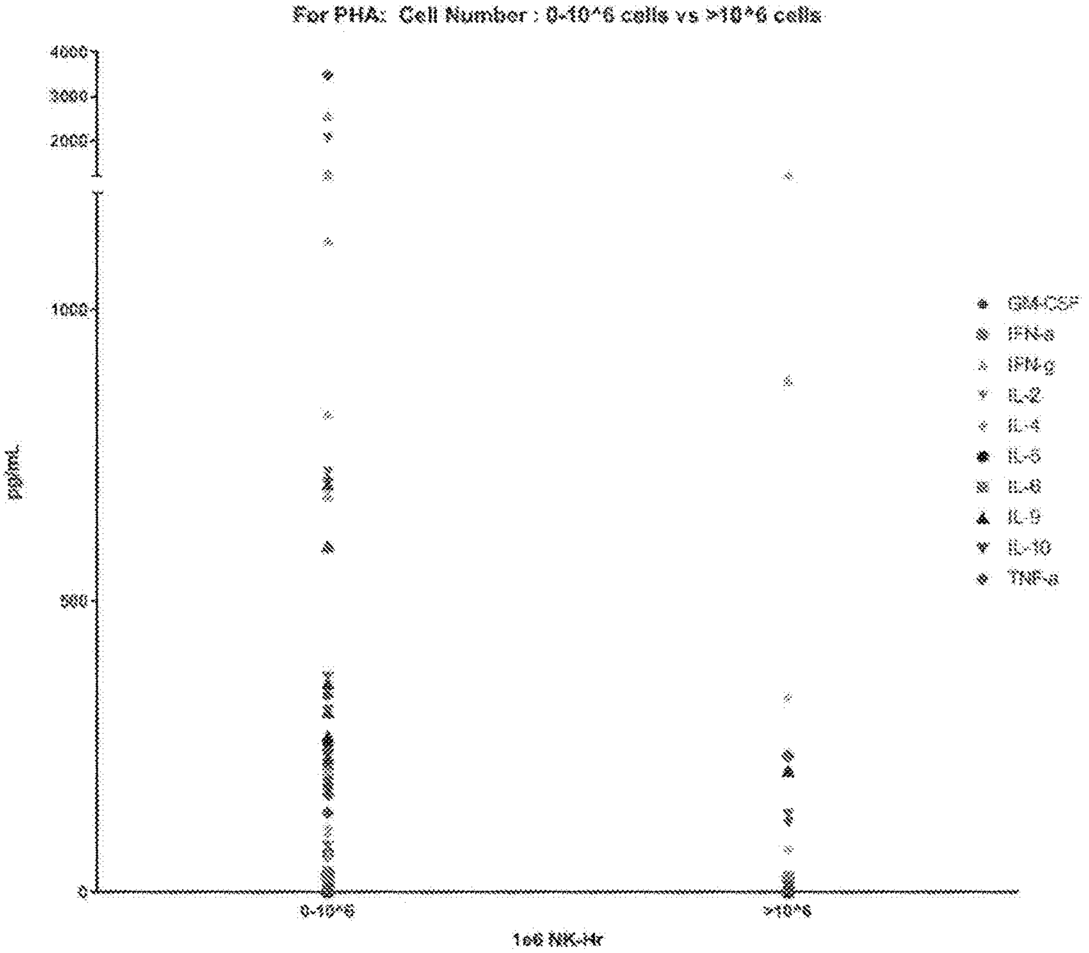
FIG. 3 provides a graph showing the analysis of results based on cell number.
Figure 4:
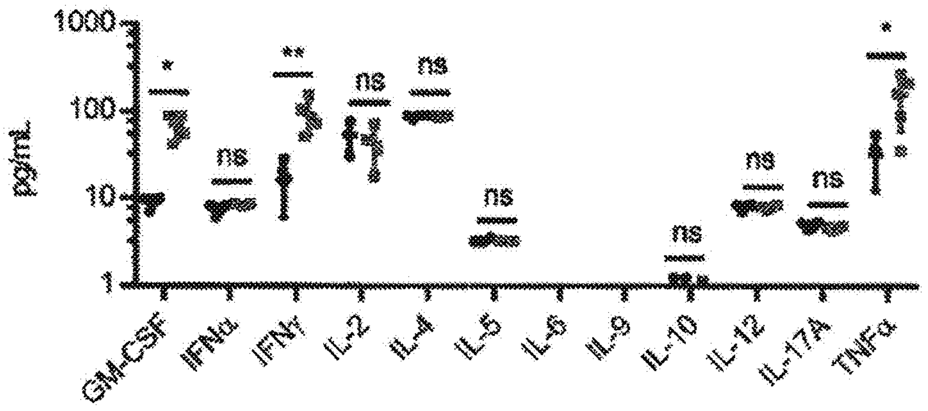
FIG. 4 provides a graph showing the results of a PHA assay of NK cells expanded with mb-IL-21 and TGF-β.
Figure 5:
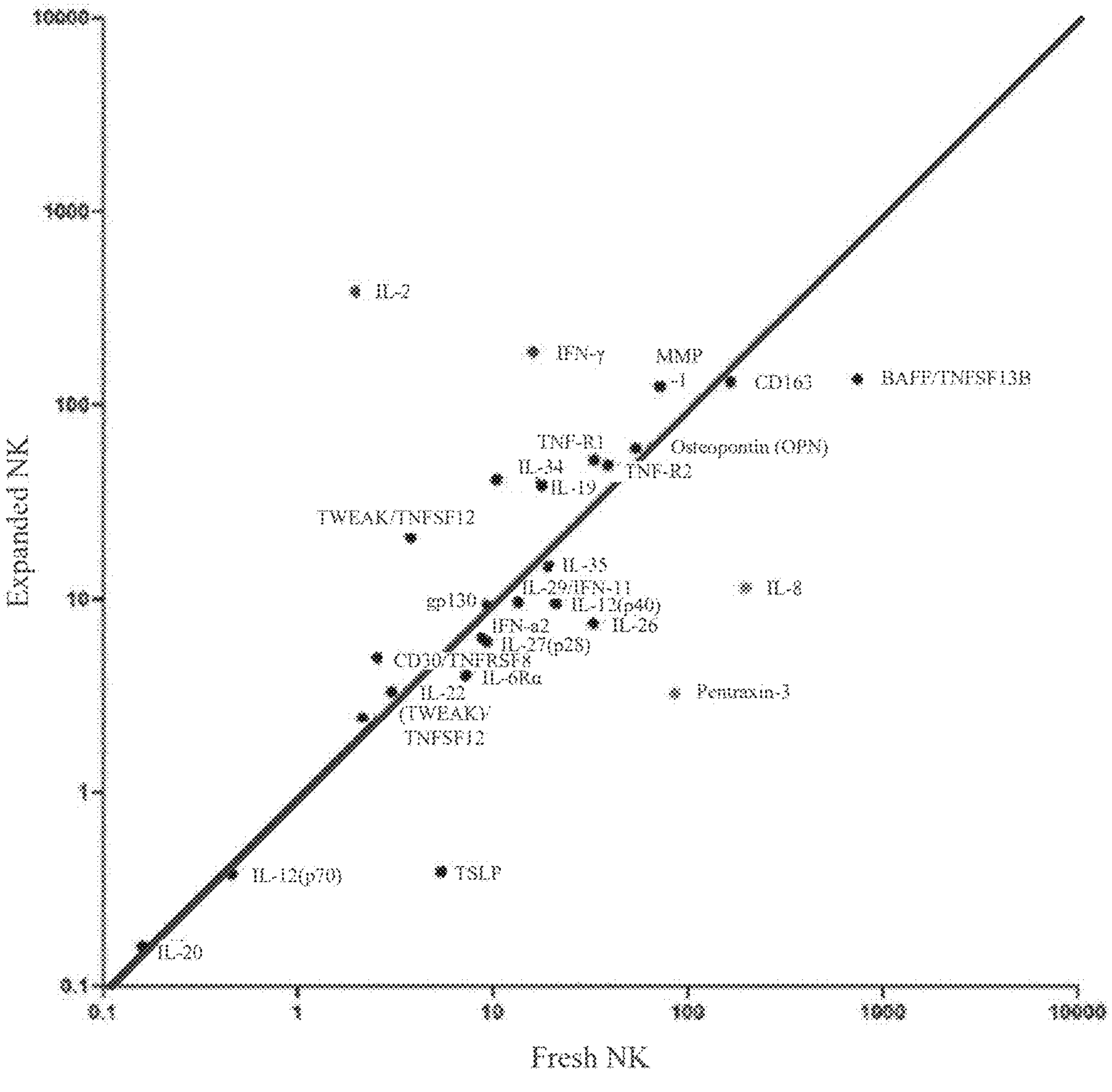
FIG. 5 provides a plot showing the correlation between freshly isolated NK cell cytokine release (induced by PHA) versus expanded NK cell cytokine release induced by PHA (in pg/million cells/hr).

FIG. 2 shows a histogram of cytokine levels achieved using a four hour incubation versus a 24 hour incubation (with 1 million NK cells). FIG. 3 shows a histogram of cytokine levels achieved using less than 1 million cells and greater than 1 million cells. These conditions were tested in order to standardize the assay. FIG. 4 shows the results of a PHA assay of NK cells expanded with mb-IL-21 and TGF-β. FIG. 5 shows the difference in cytokine profile between donor immune cells and expanded therapeutic NK cell product when induced by PHA.

Figure 6:
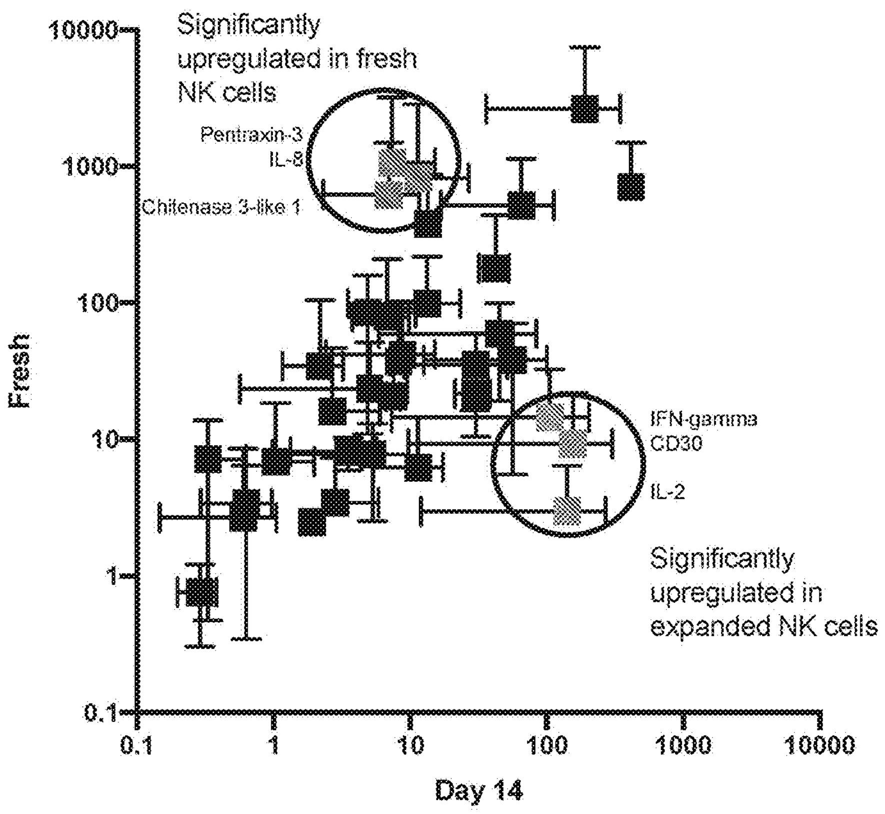
FIG. 6 provides a plot showing cytokine expression of NK cells following 1 hour stimulation by PHA in expanded (N=18) and freshly procured (N=10) NK cells.
Figure 7:
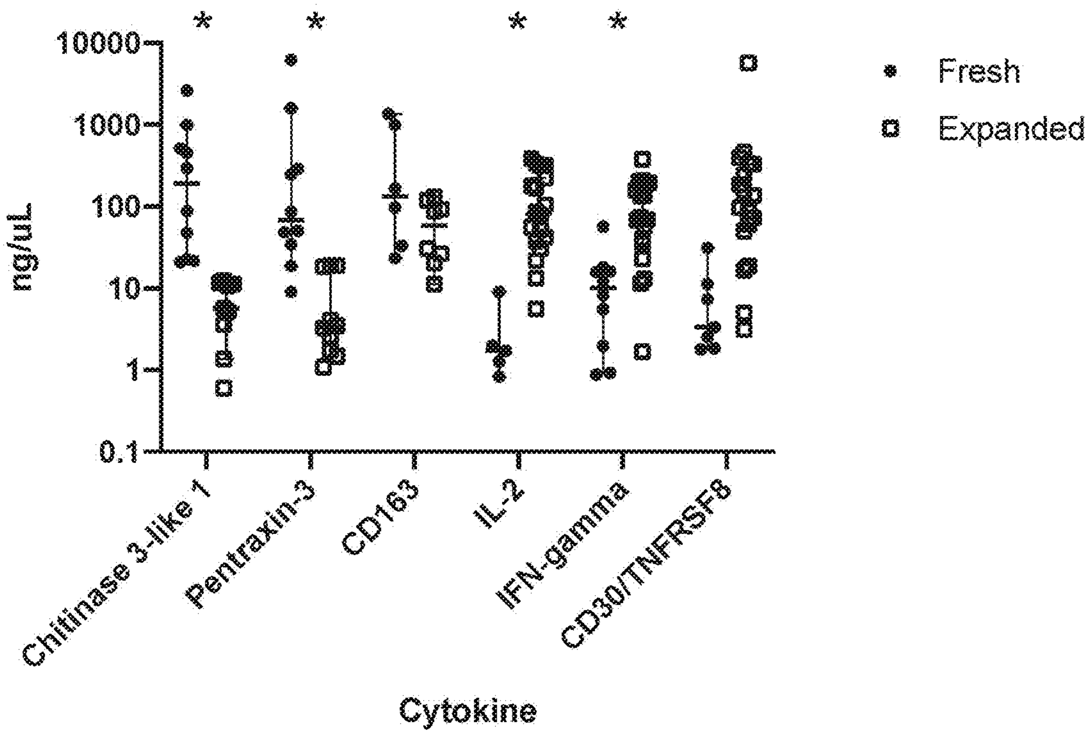
FIG. 7 shows a comparison of the concentration of cytokines expressed between freshly procured and expanded NK cells following PHA stimulation.
Figure 8:
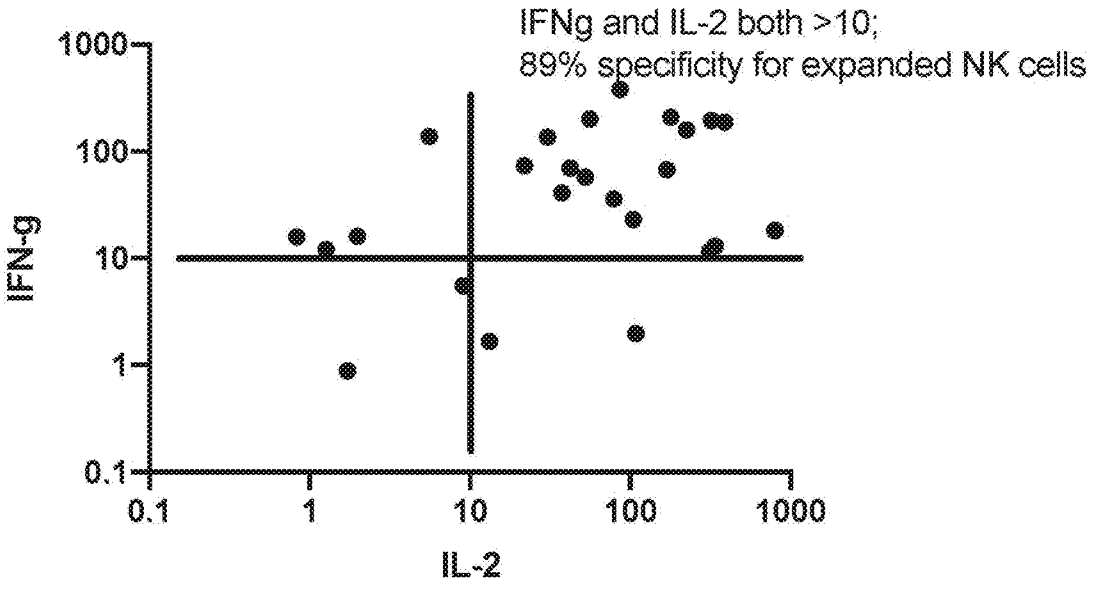
FIG. 8 provides a plot showing the specificity and sensitivity in differentiating expanded NK cells based on IFN-γ and IL-2 expression.
Figure 9:
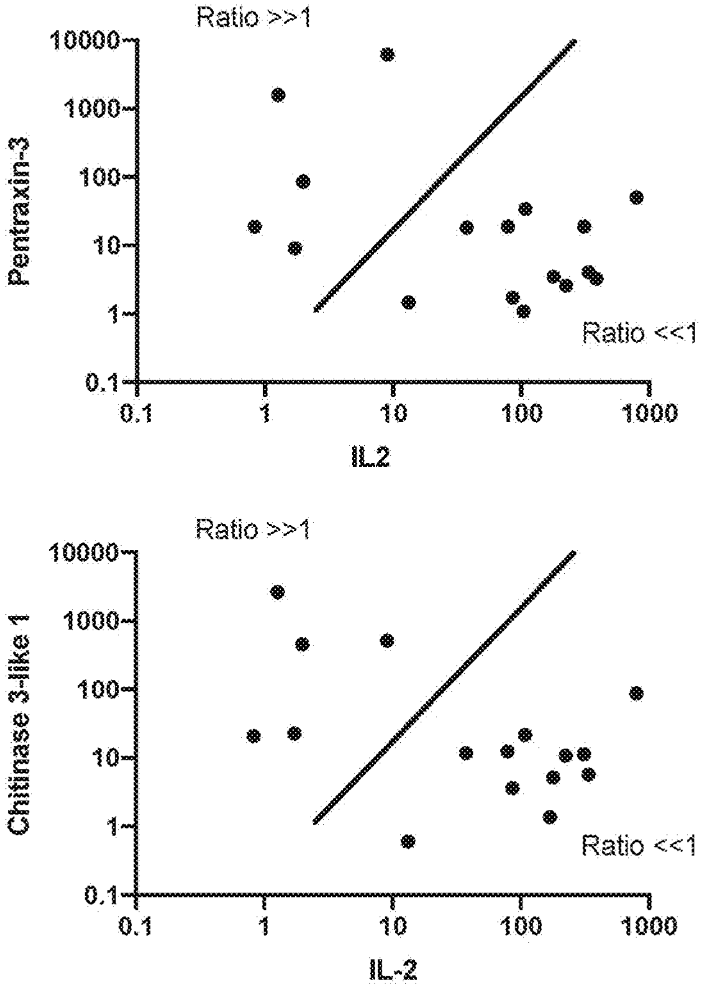
FIG. 9 shows that freshly procured NK cells and expanded NK cells can be differentiated based on IL-2 upregulation and Pentraxin-3 or chitinase 3-like 1 downregulation.
Figure 10:
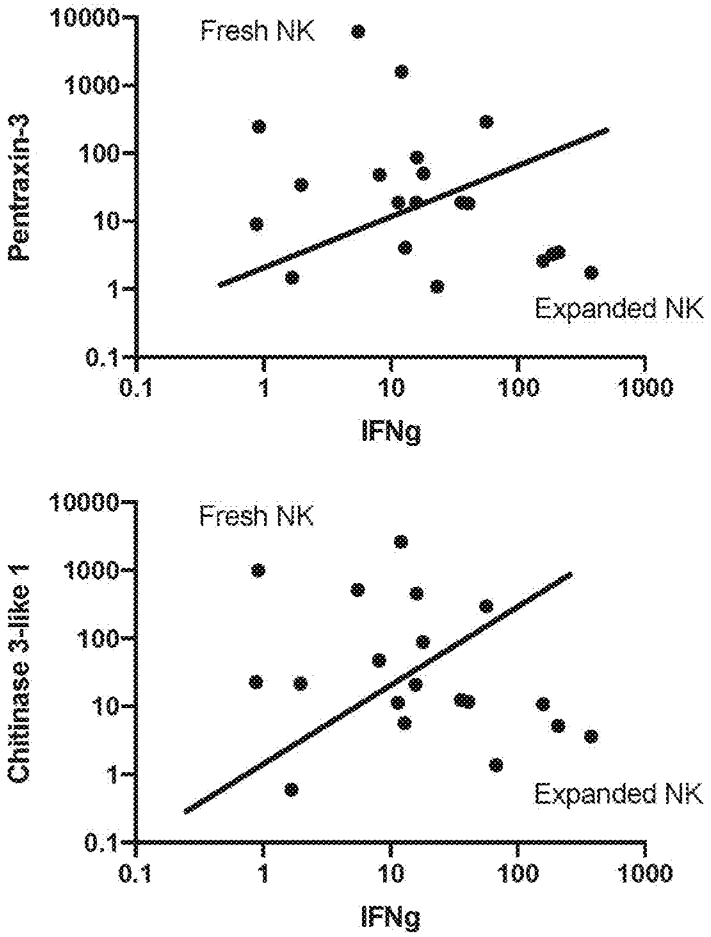
FIG. 10 shows that freshly procured NK cells and expanded NK cells can be differentiated based on IFN-γ upregulation and Pentraxin-3 or chitinase 3-like 1 downregulation.

After establishing an optimal number of cells ($10^6$) for the assay, multiple donors of fresh peripheral blood NK cells (N=10) and expanded NK cells (N=18) were stimulated with PHA to produce cytokines, and after 1 hour cytokine in the supernatant was assessed. Expression of most cytokines are similar between the two types of NK cells, but several cytokines and chemokines related to NK cell function were highly differentially expressed in response to stimulation (FIG. 6). Next the expression of 6 cytokines in fresh and expanded NK cells was measured after 1 hour stimulation with PHA. Pentraxin-3 (mean 1,062 vs 7), IL-8 (mean 821 vs 11), and Chitinase 3-like 1 (mean 620 vs 7) were highly overexpressed in fresh NK cells compared to expanded NK cells, and IFN-γ (mean 15 vs 105), IL-2 (mean 3 vs 141), and CD30 (mean9 vs. 156) were highly overexpressed in expanded NK cells compared to fresh NK cells (FIG. 7). On the basis of overexpression alone, a cut-off of expressing 10 pg/mL of both IFN-γ and IL-2 has 94% specificity (16 of 17) and 89% sensitivity (16 of 18) in differentiating expanded NK cells from fresh peripheral blood NK cells (FIG. 8). Using IL-2 (upregulated) along with a downregulated cytokine (Pentraxin-3 or Chitinase 3-like 1) was 100% sensitive and specific to differentiating expanded NK cells from fresh peripheral blood NK cells with expression ratios (downregulated:IL-2)>1 for fresh cells, and <1 for expanded cells (FIG. 9). Using IFNg (upregulated) along with a downregulated cytokines (Pentraxin-3 or Chitinase 3-like 1) was 95% effective in differentiating expanded NK cells from fresh peripheral blood NK cells. Combinations of multiple upregulated and downregulated cytokines could be used for increasing sensitivity and specificity of defined types (FIG. 10).

Unless defined otherwise, all technical and scientific terms used herein have the same meanings as commonly understood by one of skill in the art to which the disclosed invention belongs. Publications cited herein and the materials for which they are cited are specifically incorporated by reference. However, it should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Those skilled in the art will recognize, or be able to ascertain using no more than routine experimentation, many equivalents to the specific embodiments of the invention described herein. While the invention has been described with reference to particular embodiments and implementations, it will understood that various changes and additional variations may be made and equivalents may be substituted for elements thereof without departing from the scope of the invention or the inventive concept thereof. In addition, many modifications may be made to adapt a particular situation or device to the teachings of the invention without departing from the essential scope thereof. Such equivalents are intended to be encompassed by the following claims. It is intended that the invention not be limited to the particular implementations disclosed herein, but that the invention will include all implementations falling within the scope of the appended claims.

The invention claimed is:

1. A method of assaying the potency of an interleukin-21 (IL-21) expanded natural killer (NK) cell, comprising (i) contacting an IL-21 expanded NK cell with an effective amount of a stimulating agent;

(ii) detecting the amount of a plurality of cytokines produced by the IL-21 expanded NK cell of step (i);

(iii) comparing the amount of cytokines produced by the IL-21 expanded NK cell of step (i) to a control level, thereby showing the effector function of the IL-21 expanded NK cell; and (iv) selecting a potent IL-21 expanded NK cell of step (iii) based on the amount of cytokines detected in step (ii), wherein the plurality of cytokines of step (ii) comprises IL-2, interferon gamma (IFNy), Pentraxin-3, and Chitinase 3-like 1;wherein the potent IL-21 expanded NK cell exhibits an upregulation of IL-2 and IFN gamma, and a downregulation of Pentraxin-3 and Chitinase 3-like 1 differentiates the IL-21 expanded NK cell from a fresh NK cell when compared to the control level.

2. The method of claim 1, wherein the stimulating agent comprises phytohemagglutinin (PHA), phorbol myristate acetate (PMA)/ionomycin, concanavalin A (Con A), lipopolysaccharide (LPS), and/or pokeweed mitogen (PWM).

3. The method of claim 1, wherein the amount of cytokines is detected using an immunoassay.

4. The method of claim 1, wherein the plurality of cytokines further comprises one or more of IL-6, B cell activating factor/tumor necrosis factor (TNF) ligand superfamily member 13B (BAFF/TNFSF13B), TNF-a, cluster of differentiation (CD) 163 (CD163), CD30/TNFRSF8, gp130, IFN-a2, IL-6Ra, IL-8, IL-10, IL-11, IL-12 (p40), IL-12 (p70), IL-20, IL-22, IL-26, IL-29/IFN-11, IL-32, IL-34, IL-35, matrix metalloproteinase-1 (MMP-1), Osteocalcin, Osteopontin (OPN), tumor necrosis factor (TNF)-receptor 1 (TNF-R1), TNF-R2, thymic stromal lymphopoetin (TSLP), granulocyte-macrophage colony-stimulating factor (GM-CSF), leukemia inhibitory factor (LIF), and the chemokines macrophage inflammatory protein (MIP)-1a (MIP-1α), MIP-1b, RANTES, and/or TNF-related weak inducer of apoptosis (TWEAK)/TNF superfamily member 12 (TWEAK/TNFSF12).

5. The method of claim 4, wherein the plurality of cytokines further comprises CD30.

6. The method of claim 2, wherein the stimulating agent comprises PHA.

7. The method of claim 1, wherein the IL-21 expanded NK cell is contacted with an effective amount of the stimulating agent for at least 4 hours.

8. The method of claim 1, wherein the stimulating agent is provided at a concentration of 5 μg/mL or 6 μg/mL.

9. An immunotherapy method comprising:

(a) performing the method of claim 1 on multiple IL-21 expanded NK cells to select a potent IL-21 expanded NK cell; and (b) administering a therapeutically effective amount of the selected potent IL-21 expanded NK cell of step (a) to a subject in need thereof as an immunotherapeutic.

10. The immunotherapy method of claim 9, further comprising extracting the multiple IL-21 expanded NK cells from an allogeneic or autologous donor prior to expanding and assaying the potency of the multiple IL-21 expanded NK cells.

11. The immunotherapy method of claim 9, further comprising genetically altering the multiple IL-21 expanded NK cells or the potent IL-21 expanded NK cell to respond to a specified antigen.

12. The immunotherapy method of claim 9, further comprising genetically altering the multiple IL-21 expanded NK cells or the potent IL-21 expanded NK cell to present a chimeric antigen receptor (CAR).

13. A method of treating, inhibiting, reducing, and/or ameliorating a cancer and/or metastasis in a subject comprising:

selecting a potent IL-21 expanded NK cell by performing the method of claim 1; and administering to the subject a therapeutically effective amount of the potent IL-21 expanded NK cell.

14. The method of claim 13, further comprising extracting the IL-21 expanded NK cell from an allogeneic or autologous donor prior to expanding and assaying the potency of the IL-21 expanded NK cell.

* * * * *